United States Patent [19]

Swanson

[11] 4,381,663

[45] May 3, 1983

[54] FLUID OSCILLATION MATERIALS TESTING APPARATUS AND METHODS

[75] Inventor: Wilbur M. Swanson, St. Louis County, Mo.

[73] Assignee: Washington University, St. Louis, Mo.

[21] Appl. No.: 241,078

[22] Filed: Mar. 6, 1981

[51] Int. Cl.³ .............................................. G01N 3/36
[52] U.S. Cl. ......................................... 73/37; 73/168; 73/812
[58] Field of Search ................. 73/812, 811, 810, 809, 73/808, 816, 37, 168; 128/697

[56] References Cited

U.S. PATENT DOCUMENTS 3,173,372  3/1965  Baldwin .............................. 73/37 X
3,911,725  10/1975  Selivanov et al. .................. 73/37 X Primary Examiner—Jerry W. Myracle
Attorney, Agent, or Firm—Kalish & Gilster

[57] ABSTRACT

Apparatus and methods for durability (fatigue) testing of various samples (materials, valves, components and other objects) involves use of a test fixture for clamping a sample to be tested in a closed fluid environment and providing fluid passages on opposite sides of the object to be tested through which a bellows-actuated fluid oscillator causes axial oscillating flow of fluid, causing the sample to undergo repeated bidirectional axial pressures producing flexing in the case of a membrane of elastic material or repeated closing and opening in the case of a valve, etc., in response to oscillation of the fluid in the passages. The device is particularly suited for "blister testing" of elastomers and for life testing of prosthetic heart valves and other valves.

19 Claims, 13 Drawing Figures

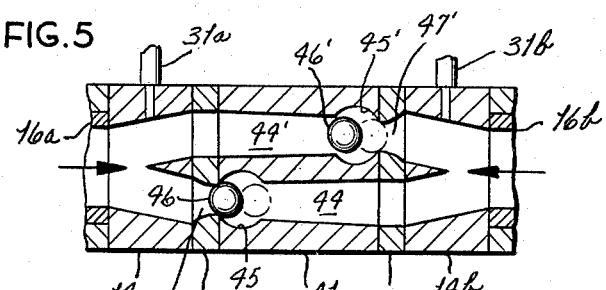
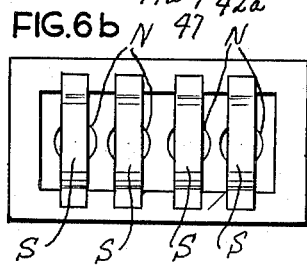
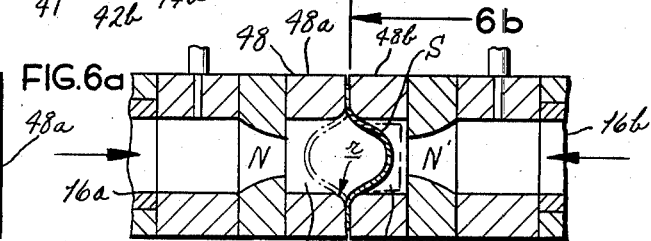
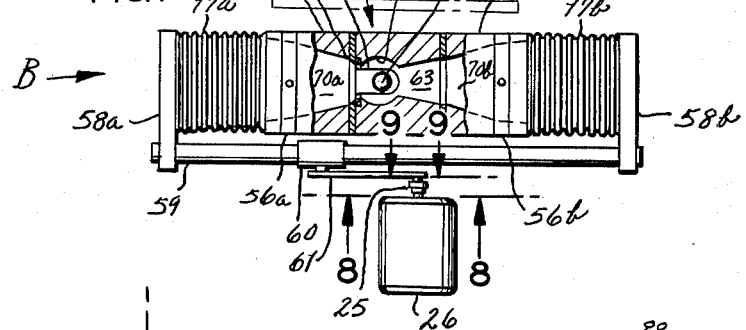
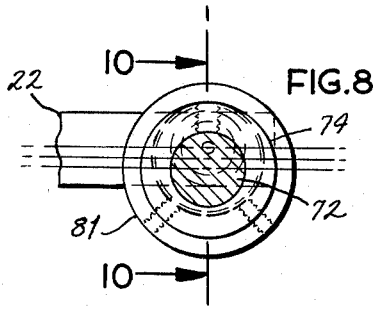
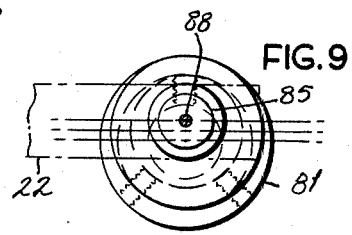
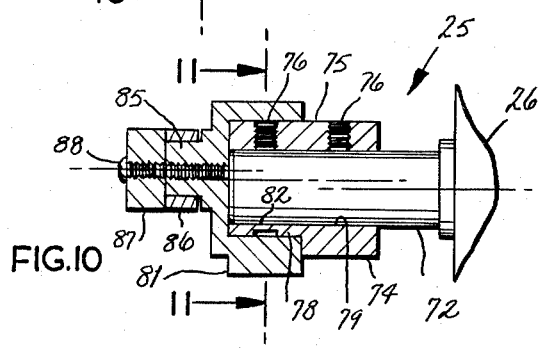
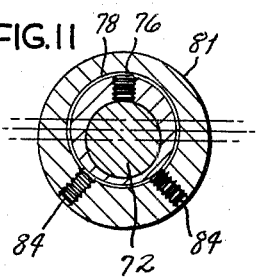

FLUID OSCILLATION MATERIALS TESTING APPARATUS AND METHODS

BACKGROUND AND SUMMARY OF THE INVENTION

The present invention relates to the testing of materials and, more particularly, to apparatus and methods for testing of samples by exposure of same to oscillating fluids.

The invention described herein was made in the course of work under a grant or award from the Department of Health, Education, and Welfare.

In the broad field of materials testing, it is known to repetitively actuate, stretch, flex, bend, or otherwise stress various materials, valves, components and other objects to determine durability, dependability and otherwise determine their suitability for particular applications. Thus, a type of durability testing is to cause the repetitive stressing of an object under test until fatigue causes failure thereof.

However, in certain kinds of test applications, it is desirable to isolate the test sample from the environment. Certain materials or devices which, during normal use, are exposed to certain fluids, will not be accurately tested if merely flexed or operated in a normal atmospheric environment. Desirably, such samples, if they are to be given truly representative durability (fatigue) tests, should be tested while immersed in a fluid to which they would be exposed in normal use.

A particular need arises in the durability-fatigue testing of biological tissue prosthetic heart valves. To be tested properly, such heart valves should be conducted in a sterile human blood plasma environment at normal body temperature, 37° C.

Accordingly, it is an object of the present invention to provide an improved apparatus for materials testing, and, more paticularly, to provide a system for making closed durability (fatigue) tests.

A further object of the invention is the provision of such apparatus and methods of testing of various samples, including without limitation elastic materials, valves, components, and other objects.

A further object of the invention is the provision of such apparatus and methods for testing of prosthetic heart valves in a sterile blood plasma, or other body fluid environment at body temperature.

Another object of the invention is the provision of such testing apparatus and methods for carrying out the testing of a sample under test, whether such be a material, valve, component, or the like, in a preselected fluid medium.

Yet another object of the invention is the provision of such testing apparatus and methods which provide repetitively stressing or operation at a high frequency, such as much greater than that at which the sample under test would be flexed in normal use, thereby greatly shortening the life testing of the sample.

A further object of the invention is the provision of such testing apparatus and methods which allow a plurality of samples to be tested at one time.

A still further object of the invention is the provision of such testing apparatus and methods which greatly minimizes test volume while requiring very little input power.

Among still other objects of the invention may be noted the provision of such testing apparatus and methods which are mechanically simple; which provide a wide range of testing conditions, including different temperatures, pressures, frequencies, stresses; which are extremely reliable in operation; and which avoid improper testing conditions.

Further objects of the invention include the provision of testing apparatus which provides testing in a completely sealed fluid environment; which provides extreme economy of use of fluids; which provides very high test versatility and ease of insertion and removal of test samples; which provides high accessibility as well as visibility of test samples; in which test fluid is easily filled or emptied; and which is easily cleaned.

Among other objects of the invention are the provision of such apparatus which exposes test fluid to extremely limited surface areas, and which areas of the apparatus provides little friction of test fluid with consequent negligible heating of fluid.

Other objects and features will be in part apparent and in part pointed out hereinbelow.

BRIEF DESCRIPTION OF THE DRAWINGS

FIG. 5 is a longitudinal cross-section of a test fixture of the apparatus, as configured for testing two ball valves.

FIG. 6A is a longitudinal cross-section of a test fixture of the invention configured for providing a reversing flexure test of material strip samples.

FIG. 6B is a transverse cross-section of the test fixture of FIG. 6A, as taken along line 6b—6b thereof.

FIG. 7 is a plan view, partially in cross-section, of an alternative embodiment of testing apparatus of the invention.

FIG. 8 is a transverse cross-section of a drive coupling unit of the invention, as taken along line 8—8 of FIG. 7.

FIG. 9 is an end elevation of the coupling unit as taken along line 9—9 of FIG. 7.

FIG. 10 is a longitudinal cross-section of the coupling unit, as taken along line 10—10 of FIG. 8.

FIG. 11 is a transverse cross-section taken along line 11—11 of FIG. 10.

Corresponding reference characters indicate corresponding parts throughout the several views of the drawings.

DESCRIPTION OF THE PREFERRED EMBODIMENT

Figure 1:
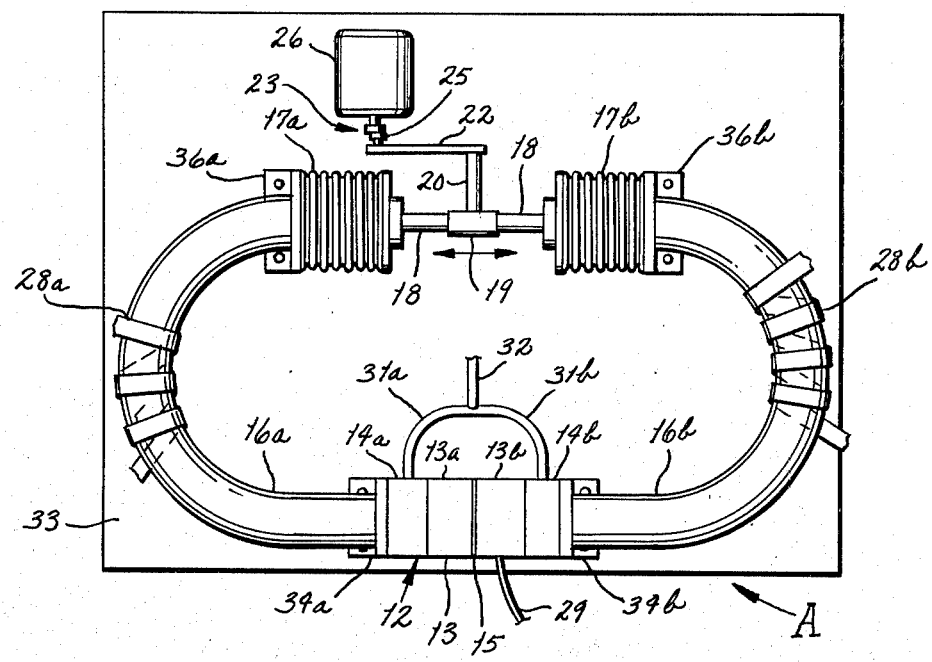
FIG. 1 is a top plan view in simplified, schematic form of testing apparatus constructed in accordance with and embodying and carrying out the present invention.

Referring now to the drawings, illustrated generally at A is a system according to a first embodiment of the invention for carrying out durability (fatigue) tests of materials, particularly membranes of an elastic material, valves, components, and other objects. In this sense, the terms "objects" or "test samples" are intended to encompass any of a variety of items which can be tested in the closed environment provided by apparatus of the invention.

In general, system A constitutes a bellows-actuated fluid oscillator for cycling fluid at high frequency, e.g., from about 200 to about 2,600 cycles per minute, in a completely closed condition for repeatedly exposing the sample under test to the action of an oscillatory fluid on opposite sides of the sample. The action involves all three of (1) forces; (2) inertia and (3) flow.

For this purpose, there is provided a test fixture generally 12 including a test jig or unit 13 having sections of sample holding blocks 13a, 13b and clamped between end or adaptor blocks 14a, 14b. A sample 15 of, for example, an elastomeric material to be biaxially stress tested, or blister tested, is clamped between sections 13a, 13b. Each of said sections 13a, 13b has a fluid passage therein. The test unit 13 is, in effect, a test chamber.

Communicating with the respective fluid passages are flow channels or conduits 16a, 16b which are in turn connected to the outer ends of respective bellows 17a, 17b. A shaft 18 interconnects the opposed inner ends of bellows 17a, 17b. Shaft 18 carries a central fitting 19 having an extension 20 connected to one end of an operating or connecting rod 22. The opposite end of said rod is interconnected with an oscillating drive mechanism generally 23 including an eccentric coupling unit 25 and an electric motor 26, the speed of which may depend upon a frequency at which the fluid can be caused to oscillate at resonant conditions explained later. Accordingly, upon rotation of motor 26 at either a desired or intrinsically determined rotational velocity, operating rod 18 will be caused to shift axially back and forth in an oscillating manner to provide alternate compression and extension, i.e., contraction and expansion of bellows 17a, 17b, whereby fluid will be caused to oscillate in phased synchronism within flow channels 16a, 16b, thereby imposing upon sample 15 alternating bidirectional fluid forces.

Wrapped around portions of flow channels 16a, 16b are lengths of heater tape 28a, 28b adapted for being suitably energized, whether continuously or on a proportional or as-needed basis, in response to the temperature of the fluid within the system interconnected as shown at 29 to a conventional thermostatic control (not shown) of commercially available type which controls the energization of heater means 28a, 28b.

Also interconnected with opposite ends of test fixture 12 and communicating with the fluid passages defined within the holding blocks 13a, 13b are respective conduits 31a, 31b which are joined at a tee connection 32. The latter is, in turn, connected to a conventional high-low pressure switch cutout (not shown) for cutting off power to motor 26 (and/or heaters 28a, 28b) in the event of either excess pressure buildup within the system or leakage, thus precluding improper testing. In this regard, the size of conduits 31a, 31b is small, being chosen to provide a relatively high impedance interconnection between holding blocks 31a, 31b for maintaining within tee connection 32 a substantially constant equilibrium pressure or average, i.e., a mean volume on each side of the tee, but providing negligible oscillating flow through conduits 31a, 31b during operation at the normal drive frequency.

Although the high-low pressure switch interconnection with tee 32 provides for cessation for limiting of operation so that operation will be within a safe or desired pressure range, as well as permitting the apparatus to be shut off in the case of a fluid leak, pressure within either or both of test blocks 13a, 13b can be similarly monitored by pressure sensing for the purpose of determining failure of a sample under test, such as rupture of a membrane sample permitting communication between the two test block halves 13a, 13b.

The entire unit may be mounted on a suitable test board 33 and with the test fixture 12 being secured to said board 33 by appropriate brackets, as at 34a, 34b. Similarly, the fixed ends of bellows 17a, 17b are interconnected with brackets 36a, 36b secured to board 33. Motor 26 is, of course, also affixed to board 33.

Figure 3A:
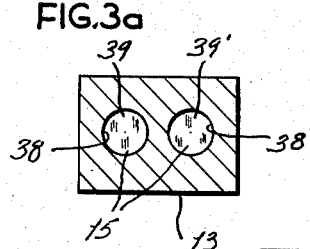
FIGS. 3A and 3B are cross-sections of a test block of the apparatus, taken along line 3—3 of FIG. 2.
Figure 3B:
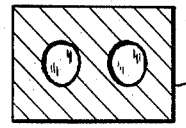
Figure 4:
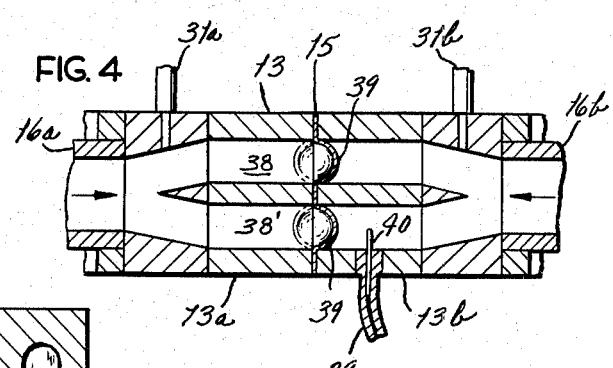
FIG. 4 is an enlarged longitudinal cross-sectional view of a test fixture of the apparatus as configured for providing a reversing flexure test of material strip samples providing a reversing biaxial stress test of material sheet or membrane samples.

Referring to FIGS. 3A, 3B and 4, test blocks 13a, 13b provide two axial passages 38, 38' therein, with sample 15 being represented by a thin membrane or layer of elastomeric material, such as synthetic resin, to be tested for durability by "blistering" the material first in one direction and then the other by the force of oscillatory flow of fluid within chambers 38, 38'. Although the cross section of each of passages 38, 38' is shown circular, it may be elliptical, as in FIG. 3B, or of other non-circular section.

Thus, in FIG. 4, it will be seen that as drive rod 18 moves to the right, compressing bellows 17b, pressure in flow channel 16b causes sections 39, 39' of sample 15 to deform or "blister" to the left, as viewed in FIG. 4, in a biaxial tensile mode. Upon the second half of the cycle, bellows 17a is compressed, i.e., contracts, to increase pressure in fluid channel 16a so that sample 15 will then "blister" in the opposite direction. There is then bidirectional blistering deformation as the fluid oscillatingly flows back and forth in conduits 38, 38'.

Without intending to limit the scope of the invention, the fluid in the system may be water, blood plasma, oils or various other liquids or gases to which it is desired to expose sample 15 during the durability testing. Such testing may be continued until rupture of one of the portions 39, 39' of the test sample occurs.

By use of temperature transfer coils 28a, 28b, the temperature within the fluid may be readily elevated above room temperatures. Such temperature is conveniently monitored by a probe 40 which protrudes into channel 38' of block 13b. More than one probe may be used. Of course, said coils 28a, 28b may be cooling coils, such as tubing for containing a coolant, and thus, it will be apparent that the drawing represents merely one of various possible cooling or heating arrangements which may be utilized for effecting heat transfer with respect to the test fluid. Conventional thermostatic control, such as through use of solenoid valves, heaters, refrigeration equipment, etc. is suitably under the control of temperature sensing device 40, which may be a thermocouple, or thermistor, etc. In this way, means are provided for maintaining the fluid in the system at a predetermined temperature. If, for example, testing of prosthetic heart valves is to be carried out in a sterile human blood plasma environment, it is maintained at 37° C., representative of normal body temperature.

Components of the system which contact the fluid, such as sterile human blood plasma, are desirably constructed of materials which are non-reacting with the fluid, such as stainless steel, nylon, "Teflon", or other synthetic resin materials. Since the system is closes, the fluid is not exposed to atmosphere or other oxidizing or non-sterile factors.

Referring to FIG. 5, a test block 41 is fitted between end blocks 14a, 14b, there being interposed at opposite ends of said block 41, adaptor blocks 42a, 42b. Block 41 provides two passages 44, 44' of diameter each reducing toward the length of the block but then opening into respective enlarged portions 45, 45' in which are located ball valves 46, 46' which are adapted to seat upon reduced diameter openings 47, 47' within adaptor blocks 42a, 42b, respectively. There are, thus, provided two ball valves which may undergo fatigue testing to determine their durability, such as by monitoring wear, sealing, etc., in response to the oscillating flow of fluid within passages 44, 44'. One may readily understand that one valve closes as the fluid shifts in one direction upon one half of the cycle, the other valve being at such time open. The situation then will be reversed as the fluid shifts in the opposite direction during the remaining half of the period of oscillation.

In this way, it is appreciated that there are provided two test-section channels for testing of two check valves. For such valve testing, the desired flow and peak closing pressures are established by adjusting the drive mechanism amplitude and frequency. FIG. 5 is merely representative of testing of one configuration of check valves. Other types of valves may be tested, as well as various other mechanical components, materials and so forth.

FIGS. 6A and 6B show the provision of a test block 48 having sections 48a, 48b between which are clampingly engaged a plurality of strips S (2, 4, or 6) of material to be flexure tested by "blowing" them back and forth at the oscillating fluid is ejected from a set of nozzles N on one side and injected into a set N' on the opposite side, and conversely with a reverse of the oscillating mechanism. As fluid oscillates, flowing back and forth within chambers 52a, 52b, the test sample or section is caused to buckle in a semi-circular configuration as the oscillating fluid flexes the elastomeric material over a specified radius r.

Figure 2:
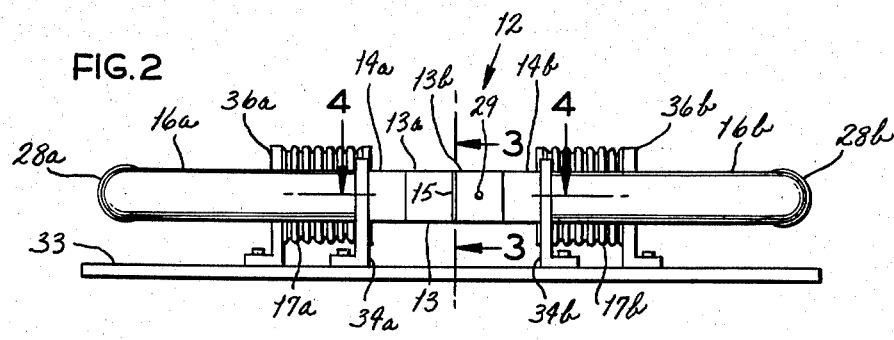
FIG. 2 is a front elevation of the testing apparatus of FIG. 1 particularly demonstrative of a test fixture thereof.

Referring now to FIG. 7, a second embodiment of the invention is designated generally at B provides numerous advantages when compared to embodiment A. Bellows 17a, 17b are located at opposite ends of a test fixture or chamber generally designated 54. Fixture 54 comprises a center test block and opposite end blocks 55a, 55b which are in turn secured to adaptor blocks 56a, 56b affixed to the inner ends of bellows 17a, 17b. The test chamber-remote ends of bellows 17a, 17b are secured to respective blocks 58a, 58b, respectively, interconnected by a common actuating shaft 59 having a fitting 60 to which is connected an operating or connecting rod 61. The latter is connected by coupling unit 25 to motor 26. Test block or unit 54 is affixed to a suitable base such as that designated at 33 in FIGS. 1 and 2, and to which is also mounted motor 26.

Test unit or block 54 preferably comprises compressibly joined sections of a rectangular block of visually nonocclusive material such as preferably polymethylmethacrylate (PMMA), allowing observation of the operation and condition of heart valves or other test samples located therein. For heart or other biological and leaflet valve testing in biological fluids, the materials of components containing the fluid are preferably stainless steel, nickel, and the above-noted PMMA.

The test unit 54 may have two passages and valves as illustrated in FIG. 7 which are identical to the test passages and the blocks of FIG. 5, which constitutes a top view of the test section of the apparatus illustrated in FIG. 7, but greater numbers of valves can be similarly tested.

Provision is preferably made for allowing the entire unit consisting of test block 54 and bellows 17a, 17b to be removed integrally for ease of valve mounting and removal, filling of fluid, bleeding of gases, and cleaning.

Accordingly, operation of motor 26 causes oscillatory shifting of the end plates 58a, 58b of bellows 17a, 17b to provide for movement of fluid within test unit 54. There is shown in center test unit or block 54 a passage 63 which is necked down and then opens into an enlarged sinus chamber 64 in which is located the cage 65 of a prosthetic heart valve having a ball 66. Cage 65 is carried by a base flange 68 providing a seat for ball 66. Passages 70a, 70b are provided within end blocks 55a, 55b each having diameter which enlarges in the direction of the respective bellows. High impedance interconnecting connections 31a, 31b may be made with these passages in adaptor blocks 56a, 56b for the purpose previously described, being connected by a similar tee connection (not shown) connected to a high-low pressure switch, all as discussed above.

The configuration provided for embodiment B is extremely compact, incorporating a very small amount of fluid which is caused to flow oscillatingly back and forth through passage 70a, 70b for alternately opening and closing ball 66 against its seat 68, thereby providing for durability (fatigue) testing of the prosthetic heart valve.

The fluid is preferably sterile blood plasma, serum or other biological fluids or solutions.

Accordingly, the extreme compactness of this embodiment greatly minimizes the volume of such fluid, e.g., requiring only 850 ml of such biological fluids.

Because the fluid is exposed to such a limited surface area of the apparatus, there is very little friction as the test fluid oscillates therein, with consequent negligible frictional heating of fluid.

Selective heating or cooling of the test fixture may be provided as representatively shown heat transfer means, e.g., a heating or cooling device 71, positioned near test unit 64. The entire embodiment B, or at least such portions as are to be heated or cooled by means 71, are preferably enclosed in a suitable thermal housing providing thermal insulation with respect to the ambient environment. There is, thus, provided means for heating or cooling the new test apparatus of embodiment B to maintain a predetermined temperature within the flow channel on opposite sides of the sample under test.

The low fluid and mechanical mass of this embodiment provides oscillation at a high resonant frequency of 1000–2000 cycles per minute noted below, with very little driving power, e.g., less than one watt.

Referring now to FIGS. 8–11, the features of drive coupling unit 25 are demonstrated. Fundamentally, said drive coupling unit 25 provides a variable-throw crank drive to provide a crank arm of adjustable length for connection of connecting rod 22 to the drive shaft 72 of motor 26, as shown at 72 (FIG. 10). Unit 25 includes a first eccentric shaft coupling member 74 including a sleeve portion 75 having set screws 76 for securement to motor shaft 72. A hub portion 78 is machined eccentrically with respect to the axis of a bore 79 which receives motor shaft 72. A second eccentric coupling member 81 is bored, as at 82, to provide a sliding fit upon eccentric hub portion 78. Bore 82 is eccentric with respect to the cylindrical body of member 81 to produce partial balance of coupling unit 25 when running and to provide greater tapping depths for clamping set screws 84, by which member 81 is clampingly secured to member 74. The body of member 81 includes an extension 85 providing a final drive hub for connecting rod end 86, secured by a retaining member 87 held in place by a screw 88. Member 81 is machined such that the drive hub 85 has an eccentricity relative to the axis of bore 82 equal to that of eccentric 78 with respect to the axis of bore 79. Accordingly, member 81 may be rotated relative to eccentric 78 and can then be secured to eccentric 78 in desired position by set screws 84, resulting in an effective crank arm for connection of connecting rod end 86 to motor shaft 72. Such crank arm may, thus, vary from zero through twice the eccentricity of eccentric 81 with respect to the axis of bore 79. Accordingly, one may adjust the drive unit to provide a predetermined magnitude of oscillation by varying the crank arm or throw to the extent one may desire.

A major advantage of apparatus of the invention is that it provides a natural frequency of oscillation determined by the spring rate, k, of the bellows and the mass, m, of the fluid in it: $\omega = \sqrt{k/m}$. The flow of resistance can be expected to be relatively small with respect to the inertive reactance in the system so that the resonant frequency is essentially equal to this natural frequency. For example, the conditions of k = 72,000 N/meter (400 lbf/in.), and m = 4 kg (2 lbm) give $\omega$ = 134/sec or f = 1280 cpm. Very little power is then consumed by motor 26 when driving the apparatus at this frequency. The spring rate k for the test embodiment A illustrated in FIGS. 1 and 2 would be the sum of the bellows and sample spring rates for the desired test conditions. These considerations are all the more clearly applicable to the even more compact system of embodiment B shown in FIG. 7, which attains even higher oscillation frequency at resonance, as well as greater efficiency.

Another important advantage of a system of the invention is that it is completely sealed, there being no contact by the test fluid with the ambient environment. As an illustration of this advantage, the new testing apparatus provides the first durability-fatigue testing system capable of testing biological tissue prosthetic heart valves in a sterile human blood plasma environment at 37° C. An accompanying advantage is the small volume of fluid required for a test, especially for embodiment B.

Although embodiments of the invention are illustrated as testing only a single valve, or two valves, or only two sections of a single elastomeric test sample, test sections of blocks of the apparatus may be adapted to accept more than two samples, such as four or even a greater number, as may be dependent upon the type of test to be conducted.

In view of the foregoing, it will be seen that the several objects of the invention and other advantages are achieved by the new constructions which have been described.

Although the foregoing includes the description of the best mode of the embodiments contemplated carrying out the invention, various modifications are contemplated.

As various modifications could be made in the constructions and methods herein described and illustrated without departing from the scope of the invention, it is intended that all matter contained in the foregoing description or shown in the accompanying drawings shall be interpreted as illustrative rather than limiting.

What is claimed is:

1. Materials testing apparatus for testing of a test sample by application of repeated oscillatory forces or fluid motion thereon, characterized by means defining fluid passages on opposite sides of said test sample, means for clamping said test sample between said fluid passages, and fluid oscillation means for causing axial oscillating flow of fluid within said passages relative to the opposite sides of said test sample whereby said test sample is caused to undergo repeated oscillating forces or motions produced by oscillation of said fluid, said fluid oscillatory means comprising a pair of bellows connected respectively to said fluid passages at opposite ends of a test fixture clamping said test sample, and defining said fluid passages, said bellows being configured for alternate contraction and expansion to cause oscillating movement of fluid within said passages, and drive means for causing repeated contraction and expansion of said bellows, said test fixture and said pair of bellows being aligned along a single axis with said test fixture being interposed between said bellows, said fluid passages defining a closed fluid environment for testing of said test sample, said fluid passages extending axially from opposite sides of said test sample for providing axial oscillatory forces or motions upon said test sample.

2. Materials testing apparatus according to claim 1 and further characterized by said test sample comprising a valve, said oscillatory forces causing repeated actuation of said valve.

3. Materials testing apparatus according to claim 2 and further characterized by said valve comprising a prosthetic heart valve.

4. Materials testing apparatus according to claim 3 and further characterized by said fluid comprising blood plasma.

5. Materials testing apparatus according to claim 1 and further characterized by said test sample comprising a layer or sheet or membrane of elastomeric material transversely with respect to said passages, said passages extending on opposite sides of said layer, said fluid oscillation causing deformation or biaxial blister stressing of said material.

6. Materials testing apparatus according to claim 1 and further characterized by temperature control means for providing heat transfer with respect to said fluid for maintaining same at a predetermined temperature.

7. Materials testing apparatus according to claim 6 and further characterized by said temperature control means including at least one temperature probe extending into at least one of said passages and heat transfer means proximate said passages and controlled by said temperature sensing means for providing heat transfer with respect to fluid in said passages.

8. Materials testing apparatus according to claim 1 and further characterized by said bellows and test sample together defining a spring rate for said apparatus defining with the mass of said fluid a natural resonant frequency of oscillation providing minimal power input to said drive means and relatively rapid frequency of oscillation.

9. Materials testing apparatus according to claim 1 and further characterized by said frequency of oscillation being from about 1000 to about 2,600 cycles per minute.

10. Materials testing apparatus according to claim 1 and further characterized by inner ends of said bellows being affixed to correspond ends of said test fixture, said drive means comprising a motor including a rotatable output shaft, coupling means defining a crank arm for said shaft, a linkage extending along the length of said test fixture and interconnecting the test-block remote outer ends of said bellows with said crank arm, said linkage being connected to said crank arm for causing cyclical contraction and expansion of said bellows in response to rotation of said motor output shaft.

11. Materials testing apparatus according to claim 10 and further characterized by said coupling means including a first eccentric member mounted on said output shaft, a second eccentric member mounted on said first eccentric member, and means for selectively adjusting and fixed maintaining the relationship of said second eccentric member with respect to said first eccentric to provide a crank arm throw of selected length thereby establishing the magnitude of said fluid oscillation.

12. Materials testing apparatus for testing of heart valves or other biological test samples by exposure of same to an oscillating test fluid, said apparatus being characterized by a test fixture for mounting a test sample between fluid passages extending from opposite sides of said test sample, a pair of resilient bellows for containing said test fluid, each of said bellows having inner ends affixed to opposite ends of said test sample section in opposing relationship and communicating with respective ones of said fluid passages, means for oscillatingly driving outer ends of said bellows for alternate contraction and expansion thereof at a high intrinsic resonant frequency, $\omega$, determined by the spring rate, k, of said sample and bellows and fluid mass, m, according to the formula $\omega = \sqrt{k/m}$ thereby to oscillatingly drive said test fluid back and forth through said fluid passages for repeated exposure of said test sample to oscillating forces or motion of said test fluid, said test section and bellows having a compact, rectilinear relationship.

13. A method of durability testing of a test sample characterized by positioning a test sample for bidirectional exposure to movement of fluid, surrounding at least portions of said test sample by a fluid, and imparting rapid oscillating movement of said fluid with respect to said test sample, thereby to repeatedly expose said test sample experiences to rapidly oscillation forces or motions of said fluid, said oscillatory movement being at a frequency determined as the result of a bellows having a spring rate, said fluid having a mass to provide a design condition resonant frequency determined by the fluid mass, m, and bellows and test sample combined spring rate, k, said frequency, $\omega$, being determined by the formula $\omega = \sqrt{k/m}$, said design condition resonant frequency being from about 1000 to about 2600 cycles per minute, said method being further characterized by the volume of said fluid by enclosing said fluid within a test fixture having a chamber therethrough containing said test fluid and by using said bellows connected directly to opposite ends of said test fixture in compact, rectilinear relationship, whereby only said chamber and said bellows contain said fluid.

14. A method according to claim 13 and further characterized by said test sample being at least one valve, said oscillatory movement of fluid causing opening and closing of said valve during each cycle of oscillation.

15. A method according to claim 14 wherein said valve is a prosthetic heart valve, and said fluid is blood plasma, serum or other biological fluids or solutions, and further characterized by maintaining said fluid wholly enclosed from the atmosphere and substantially at body temperature.

16. A method according to claim 14 and further characterized by said test sample being constituted by one or more pairs of valves with individual valves of each pair being oppositely oriented, said oscillatory movement alternately closing one valve of each pair while opening the other valve of each pair.

17. A method according to claim 13 and further characterized by said test sample being at least one strip of elastomeric material, said oscillatory movement of fluid causing flexure bending of said sample strip.

18. A method according to claim 13 or 17 and further characterized by said fluid oscillation displacement causing repeated blister deformation of a sheet or membrane of elastomeric material to produce biaxial stressing.

19. A method according to claim 18 and further characterized by said deformation being carried out by causing oscillatory displacement of fluid with respect to a circular, elliptical, or non-circular area section of said sample.

* * * * *